(12) United States Patent
Wunberg et al.

(10) Patent No.: US 7,960,387 B2
(45) Date of Patent: Jun. 14, 2011

(54) 2-(3-PHENYL-2-PIPERAZINYL-3,4-DIHYDROQUINAZOLIN-4-YL)ACETIC ACIDS AS ANTIVIRAL AGENTS, ESPECIALLY AGAINST CYTOMEGALOVIRUSES

(75) Inventors: Tobias Wunberg, Solingen (DE); Judith Baumeister, Wuppertal (DE); Ulrich Betz, Reinheim (DE); Mario Jeske, Solingen (DE); Gerald Kleymann, Bad Salzuflen (DE); Thomas Lampe, Düsseldorf (DE); Susanne Nikolic, Monheim (DE); Jürgen Reefschläger, Oldenburg (DE); Rudolf Schohe-Loop, Wuppertal (DE); Frank Süβmeier, Wuppertal (DE); Holger Zimmermann, Wuppertal (DE); Rolf Grosser, Leverkusen (DE); Kerstin Henninger, Wuppertal (DE); Guy Hewlett, Wuppertal (DE); Jörg Keldenich, Wuppertal (DE); Thomas Krämer, Wuppertal (DE); Peter Nell, Wuppertal (DE); Tse-I Lin, Mechelen (BE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 818 days.

(21) Appl. No.: 10/545,453

(22) PCT Filed: Jan. 29, 2004

(86) PCT No.: PCT/EP2004/000783
§ 371 (c)(1),
(2), (4) Date: Sep. 19, 2006

(87) PCT Pub. No.: WO2004/072048
PCT Pub. Date: Aug. 26, 2004

(65) Prior Publication Data
US 2007/0066622 A1 Mar. 22, 2007

(30) Foreign Application Priority Data
Feb. 12, 2003 (DE) .................. 103 05 785

(51) Int. Cl.
A61K 31/497 (2006.01)
A61P 31/12 (2006.01)
C07D 401/04 (2006.01)
C07D 239/84 (2006.01)
(52) U.S. Cl. ................... 514/252.17; 544/284
(58) Field of Classification Search ............. 514/252.17; 544/284
See application file for complete search history.

(56) References Cited

U.S. PATENT DOCUMENTS

| 7,196,086 B2 * | 3/2007 | Wunberg et al. ......... 514/252.17 |
| 2006/0235032 A1 | 10/2006 | Wunberg |
| 2007/0185121 A1 | 8/2007 | Wunberg |
| 2007/0191387 A1 * | 8/2007 | Wunberg et al. ......... 514/252.17 |
| 2007/0281953 A1 | 12/2007 | Wunberg |
| 2008/0132515 A1 | 6/2008 | Wunberg |
| 2009/0221822 A1 | 9/2009 | Goossen |

FOREIGN PATENT DOCUMENTS

| DE | 4320347 | 12/1994 |
| WO | 9941253 | 8/1999 |

OTHER PUBLICATIONS

Wang, et al., Solid-Phase Synthesis of 3,4-Dihydroquinazoline, Tetrahedron Letters, 38(50): 8651-8654 (1997).
Saito, et al., A Facile and Efficient Carbodiimide-Mediated Synthesis of Dihydroquinazolines via a Tandem Nucleophilic Addition-Intramolecular Hetero Conjugate Addition Annulation Strategy, Tetrahedron Letters, 37(2): 209-212 (1996).

\* cited by examiner

*Primary Examiner* — James O Wilson
*Assistant Examiner* — Tamthom N Truong
(74) *Attorney, Agent, or Firm* — Thomas C. Blankinship; Nicholas J. DiCeglie, Jr.; Edwards Angell Palmer & Dodge LLP

(57) ABSTRACT

The invention relates to dihydroquinazolines and methods for the production thereof, the use thereof in the treatment and/or prophylaxis of diseases, in addition to the use thereof in the production of medicaments in the treatment and/or prophylaxis of diseases, especially for use as anti-viral agents, especially against cytomegalo viruses.

4 Claims, No Drawings

2-(3-PHENYL-2-PIPERAZINYL-3,4-DIHYDROQUINAZOLIN-4-YL)ACETIC ACIDS AS ANTIVIRAL AGENTS, ESPECIALLY AGAINST CYTOMEGALOVIRUSES

The present invention relates to dihydroquinazolines and processes for preparing them, their use for the treatment and/or prophylaxis of diseases and their use for preparing medicaments for the treatment and/or prophylaxis of diseases, in particular for use as antiviral agents, in particular against cytomegaloviruses.

The synthesis of dihydroquinazolines is described in Saito T. et al. *Tetrahedron Lett.*, 1996, 37, 209-212 and in Wang F. et al. *Tetrahedron Lett.*, 1997, 38, 8651-8654.

Agents with antiviral activity and a different structure are available on the market; however, currently available therapies using ganciclovir, valganciclovir, foscarnet and cidofovir are associated with severe side-effects, for example nephrotoxicity, neutropenia or thrombocytopenia. Additionally, it is always possible for resistance to develop. Novel agents for an effective therapy are therefore desirable.

One object of the present invention is therefore to provide novel compounds having the same or improved antiviral action for the treatment of viral infective diseases in humans and animals.

It has been found, surprisingly, that the dihydroquinazolines described in the present invention have antiviral action.

The present invention provides compounds of the formula

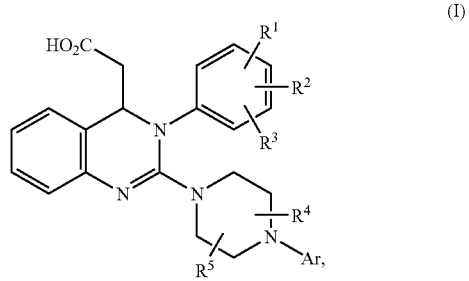

(I)

in which

Ar represents aryl which may be substituted by 1 to 3 substituents, where the substituents are selected independently of one another from the group consisting of alkyl, alkoxy, formyl, carboxyl, alkylcarbonyl, alkoxycarbonyl, trifluoromethyl, halogen, cyano, hydroxyl, amino, alkylamino, aminocarbonyl and nitro,
  where alkyl may be substituted by 1 to 3 substituents, where the substituents are selected independently of one another from the group consisting of halogen, amino, alkylamino, hydroxyl and aryl,
  or two of the substituents on the aryl radical together with the carbon atoms to which they are attached form a 1,3-dioxolane, a cyclopentane ring or a cyclohexane ring, and any third substituent present is selected independently therefrom from the group mentioned, $R^1$ represents hydrogen, alkyl, alkoxy, cyano, halogen, nitro or trifluoromethyl, $R^2$ represents hydrogen, alkyl, alkoxy, cyano, halogen, nitro or trifluoromethyl, $R^3$ represents alkyl, alkoxy, cyano, halogen, nitro or trifluoromethyl or one of the radicals $R^1$, $R^2$ and $R^3$ represents hydrogen, alkyl, alkoxy, cyano, halogen, nitro or trifluoromethyl and the other two together with the carbon atoms to which they are attached form a 1,3-dioxolane, a cyclopentane ring or a cyclohexane ring, $R^4$ represents hydrogen or alkyl, and $R^5$ represents hydrogen or alkyl, or the radicals $R^4$ and $R^5$ are attached to carbon atoms directly opposing each other in the piperazine ring and form a methylene bridge which is optionally substituted by 1 or 2 methyl groups, and their salts, their solvates and the solvates of their salts.

Compounds according to the invention are the compounds of the formula (I) and their salts, solvates and solvates of the salts, compounds mentioned hereinbelow as embodiment(s) and their salts, solvates and solvates of the salts, if the compounds mentioned hereinbelow, embraced by formula (I), are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereo-isomerically pure constituents can be isolated in a known manner from such mixtures of enantiomers and/or diastereomers.

If the compounds according to the invention can exist in tautomeric forms, the present invention also provides all tautomeric forms.

Salts in the context of the present invention are physiologically acceptable salts of the compounds according to the invention. Also provided, however, are salts which for their part are not suitable for pharmaceutical applications but which can be used, for example, for isolating or purifying the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of customary bases, such as, by way of example and preferably, alkali metal salts (for example sodium and potassium salts), alkaline earth metal salts (for example calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the present invention, solvates are those forms of the compounds according to the invention which form a complex in the solid or liquid state by coordination with solvent molecules. Hydrates are a special form of solvates in which the coordination takes place with water.

For the purposes of the present invention, unless specified otherwise, the substituents have the following meanings:

Alkyl per se and "alk" and "alkyl" in alkoxy, alkylamino, alkylcarbonyl and alkoxycarbonyl are a straight-chain or branched alkyl radical having generally 1 to 6, preferably 1 to 4, particularly preferably 1 to 3, carbon atoms, by way of example and preferably methyl, ethyl, n-propyl, isopropyl, tert-butyl, n-pentyl and n-hexyl.

Alkoxy is, by way of example and preferably, methoxy, ethoxy, n-propoxy, isopropoxy, tert-butoxy, n-pentoxy and n-hexoxy.

Alkylamino is an alkylamino radical having one or two alkyl substituents (chosen independently of one another), by way of example and preferably methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino.

Alkylcarbonyl is, by way of example and preferably, acetyl and propanoyl.

Alkoxycarbonyl is, by way of example and preferably, methoxycarbonyl, ethoxycarbonyl, n-propoxycarbonyl, isopropoxycarbonyl, tert-butoxycarbonyl, n-pentoxycarbonyl and n-hexoxycarbonyl.

Aryl is a mono- to tricyclic aromatic carbocyclic radical having generally 6 to 14 carbon atoms; by way of example and preferably phenyl, naphthyl and phenanthrenyl.

Halogen is fluorine, chlorine, bromine and iodine, preferably fluorine and chlorine.

A symbol * on a carbon atoms means that the compound, with respect to the configuration at this carbon atom, is present in enantiomerically pure form which, for the purposes of the present invention, is to be understood as meaning an enantiomeric excess of more than 90% (>90% ee).

Preference is given to those compounds of the formula (I) in which

Ar represents phenyl which may be substituted by 1 to 3 substituents, where the substituents are selected independently of one another from the group consisting of $C_1$-$C_6$-alkyl, $C_1$-$C_6$-alkoxy, carboxyl, $C_1$-$C_6$-alkylcarbonyl, $C_1$-$C_6$-alkoxycarbonyl, trifluoromethyl, fluorine, chlorine, bromine, cyano, hydroxyl, amino, $C_1$-$C_6$-alkylamino and nitro, or two of the substituents on the aryl radical together with the carbon atoms to which they are attached form a 1,3-dioxolane and any third substituent present is selected independently therefrom from the group mentioned, $R^1$ represents hydrogen, $C_1$-$C_3$-alkyl, $C_1$-$C_3$-alkoxy, fluorine or chlorine, $R^2$ represents hydrogen, $C_1$-$C_3$-alkyl, $C_1$-$C_3$-alkoxy, fluorine or chlorine, $R^3$ represents $C_1$-$C_4$-alkyl, cyano, fluorine, chlorine, nitro or trifluoromethyl, $R^4$ represents hydrogen or methyl and $R^5$ represents hydrogen, and to their salts, their solvates and the solvates of their salts.

Among these, particular preference is given to those compounds of the formula (I), in which Ar represents phenyl which may be substituted by 1 or 2 substituents, where the substituents are selected independently of one another from the group consisting of methyl, methoxy, fluorine and chlorine, $R^1$ represents hydrogen, methyl, methoxy, fluorine or chlorine, $R^2$ represents hydrogen, $R^3$ represents methyl, isopropyl, tert-butyl, cyano, fluorine, chlorine, nitro or trifluoromethyl, $R^4$ represents hydrogen, and $R^5$ represents hydrogen, and to their salts, their solvates and the solvates of their salts.

Among these, particular preference is also given to those compounds of the formula (I) in which Ar represents phenyl which may be substituted by 1 or 2 substituents, where the substituents are selected independently of one another from the group consisting of methyl, methoxy, fluorine and chlorine, $R^1$ represents hydrogen, methyl, methoxy, fluorine or chlorine, $R^2$ represents hydrogen, $R^3$ represents methyl, cyano, fluorine, chlorine, nitro or trifluoromethyl, $R^4$ represents hydrogen and $R^5$ represents hydrogen, and to their salts, their solvates and the solvates of their salts.

Preference is also given to those compounds of the formula (I), in which $R^1$ represents hydrogen, methyl, methoxy or fluorine.

Among these, particular preference is given to those compounds of the formula (I), in which $R^1$ represents methyl or methoxy.

Preference is also given to those compounds of the formula (I) in which $R^1$ is attached to the phenyl ring via the position ortho to the point of attachment of the phenyl ring. For the purposes of the present invention, the point of attachment of the phenyl ring substituted by radicals $R^1$, $R^2$ and $R^3$ is to be understood as meaning the carbon atom of the phenyl ring which, according to formula (I), is attached to one of the two nitrogen atoms of the dihydroquinazoline.

Particular preference is given to those compounds of the formula (I), in which $R^1$ represents methyl or methoxy and $R^1$ is attached to the phenyl ring via the position ortho to the point of attachment of the phenyl ring.

Preference is also given to those compounds of the formula (I) in which $R^2$ represents hydrogen.

Preference is also given to those compounds of the formula (I) in which $R^3$ represents trifluoromethyl, chlorine, methyl, isopropyl or tert-butyl.

Among these, particular preference is given to those compounds of the formula (I) in which $R^3$ represents trifluoromethyl, chlorine or methyl.

Preference is also given to those compounds of the formula (I) in which $R^1$ is attached to the phenyl ring via the position ortho to the point of attachment of the phenyl ring and $R^3$ is attached to the phenyl ring via the position meta to the point of attachment of the phenyl ring, which position is opposite to that of $R^1$.

Particular preference is given to those compounds of the formula (I) in which $R^1$ is attached to the phenyl ring via the position ortho to the point of attachment of the phenyl ring, $R^3$ represents trifluoromethyl, chlorine or methyl and $R^3$ is attached to the phenyl ring via the position meta to the point of attachment of the phenyl ring, which position is opposite to that of $R^1$.

Preference is also given to those compounds of the formula (I) in which $R^4$ and $R^5$ represent hydrogen.

Preference is also given to those compounds of the formula (I) in which Ar represents phenyl which may be substituted by 1 or 2 substituents, where the substituents are selected independently of one another from the group consisting of methyl, methoxy, fluorine and chlorine.

The particular radical definitions given in the respective combinations or preferred combinations of radicals are, independently of the combinations of radicals given in each case, also replaced as desired by radical definitions of other combinations.

Very particular preference is given to combinations of two or more of the preferred ranges mentioned above.

The invention furthermore provides a process for preparing the compounds of the formula (I), which comprises reacting compounds of the formula

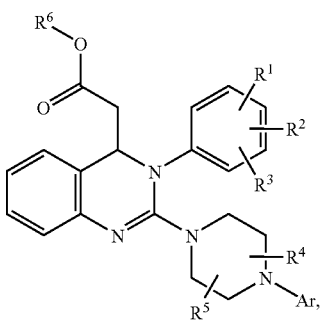

(II)

in which

Ar, $R^1$, $R^2$, $R^3$, $R^4$ and $R^5$ are as defined above and $R^6$ represents alkyl, preferably methyl or ethyl, with bases.

The reaction is generally carried out in inert solvents, preferably in a temperature range of from room temperature to the reflux temperature of the solvents, at atmospheric pressure.

Suitable bases are, for example, alkali metal hydroxides, such as sodium hydroxide, lithium hydroxide or potassium hydroxide, or alkali metal carbonates, such as caesium carbonate, sodium carbonate or potassium carbonate, if appropriate in aqueous solution; preference is given to sodium hydroxide in water.

Inert solvents are, for example, ethers, such as 1,2-dimethoxyethane, dioxane, tetrahydrofuran, glycol dimethyl ether or diethylene glycol dimethyl ether, alcohols, such as methanol, ethanol, n-propanol, isopropanol, n-butanol or tert-butanol, or mixtures of solvents; preference is given to dioxane or tetrahydrofuran.

The compounds of the formula (II) are known or can be prepared by reacting compounds of the formula

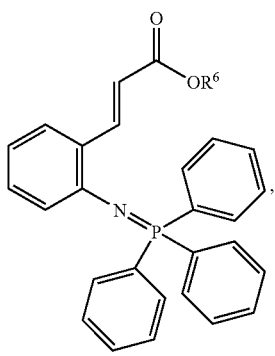

(III)

in which $R^6$ is as defined above in a two-step reaction initially with compounds of the formula

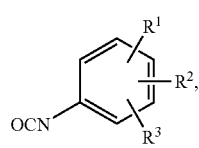

(IV)

in which $R^1$, $R^2$ and $R^3$ are as defined above and then with compounds of the formula

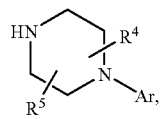

(V)

in which

Ar, $R^4$ and $R^5$ are as defined above.

Both steps of the reaction are generally carried out in inert solvents, preferably in a temperature range of from room temperature to 100° C., at atmospheric pressure. In the second step, if appropriate, silica gel is added to the reaction mixture. The reaction is preferably carried out with a work-up between the first and the second step.

Suitable inert solvents are, for example, halogenated hydrocarbons, such as methylene chloride, trichloromethane, carbon tetrachloride, trichloroethane, tetrachloroethane, 1,2-dichloroethane or trichloroethylene, ethers, such as diethyl ether, methyl tert-butyl ether, 1,2-dimethoxyethane, dioxane, tetrahydrofuran, glycol dimethyl ether or diethylene glycol dimethyl ether, hydrocarbons, such as benzene, xylene, toluene, hexane, cyclohexane or mineral oil fractions, or other solvents, such as dimethylformamide, dimethylacetamide, acetonitrile or ethyl acetate, or mixtures of solvents; preference is given to methylene chloride.

The compounds of the formula (IV) are known or can be synthesized by known processes from the corresponding starting materials.

The compounds of the formula (V) are known or can be synthesized by known processes from the corresponding starting materials, for example by a Buchwald-Hartwig reaction according to the synthesis scheme below (review in: C. G. Frost, P. Mendonca, *J. Chem. Soc., Perkin Trans I,* 1998, 2615-2623):

Buchwald-Hartwig Reaction:

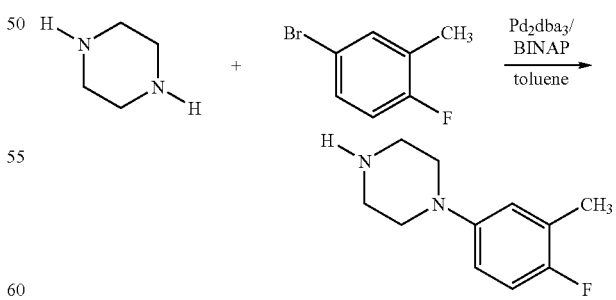

The starting materials required for this purpose are known or can be synthesized by known processes from the corresponding starting materials.

The compounds of the formula (III) are known or can be prepared by reacting compounds of the formula

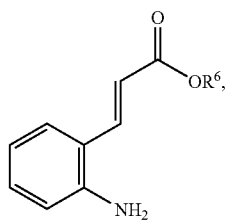

(VI)

in which

R<sup>6</sup> is as defined above with triphenylphosphine and carbon tetrachloride.

The reaction is generally carried out in inert solvents, in the presence of a base, preferably in a temperature range of from room temperature to 50° C., at atmospheric pressure.

Suitable inert solvents are, for example, ethers, such as diethyl ether, methyl tert-butyl ether, 1,2-dimethoxyethane, dioxane, tetrahydrofuran, glycol dimethyl ether or diethylene glycol dimethyl ether, hydrocarbons, such as benzene, xylene, toluene, hexane, cyclohexane or mineral oil fractions, or other solvents, such as dimethylformamide, dimethylacetamide, acetonitrile or pyridine; preference is given to acetonitrile.

Suitable bases are, for example, alkali metal and alkaline earth metal carbonates, such as caesium carbonate, sodium carbonate or potassium carbonate, or amines, such as triethylamine, diisopropylethylamine, N-methylmorpholine or pyridine; preference is given to triethylamine.

The compounds of the formula (VI) are known or can be synthesized by known processes from the corresponding starting materials.

The preparation of the compounds according to the invention can be illustrated by the synthesis scheme below.

Synthesis Scheme:

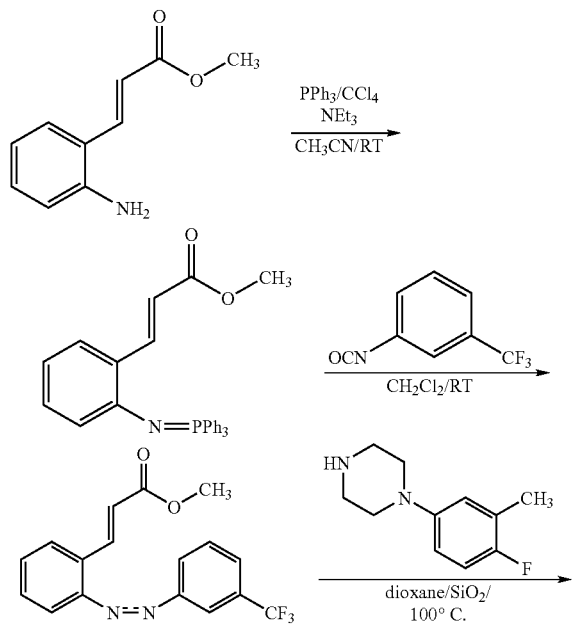

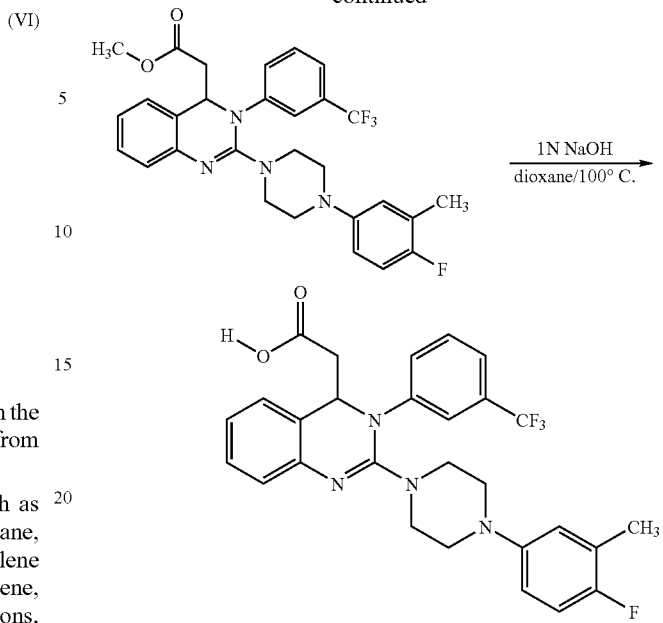

The compounds of the general formula (I) according to the invention show a surprising range of effects which could not have been predicted. They show an antiviral effect on representatives of the group of the *Herpes viridae* (Herpes viruses), especially on cytomegaloviruses (CMV), in particular on human cytomegalovirus (HCMV).

Areas of indication which may be mentioned by way of example are:

1) Treatment and prophylaxis of HCMV infections in AIDS patients (retinitis, pneumonitis, gastrointestinal infections).
2) Treatment and prophylaxis of cytomegalovirus infections in bone-marrow and organ transplantations which develop often life-threatening HCMV pneumonitis or encephalitis, and gastrointestinal and systemic HCMV infections.
3) Treatment and prophylaxis of HCMV infections in neonates and infants.
4) Treatment of an acute HCMV infection in pregnant women.
5) Treatment of HCMV infection in immunosuppressed patients associated with cancer and cancer therapy.

The present invention furthermore provides the use of the compounds according to the invention for the treatment and/or prophylaxis of diseases, especially viral infections, in particular with the viruses mentioned above, and the infective diseases caused thereby. Hereinbelow, viral infection is to be understood as meaning both an infection with a virus and a disease caused by an infection with a virus.

The present invention furthermore provides the use of the compounds according to the invention for the treatment and/or prophylaxis of disorders, in particular the disorders mentioned above.

The present invention furthermore provides the use of the compounds according to the invention for preparing a medicament for the treatment and/or prophylaxis of disorders, in particular the disorders mentioned above.

The compounds according to the invention are preferably used for preparing medicaments suitable for the prophylaxis and/or treatment of infections with a representative of the group *Herpes viridae*, in particular a cytomegalovirus, in particular the human cytomegalovirus.

The present invention furthermore provides a method for the treatment and/or prophylaxis of disorders, in particular the disorders mentioned above, using an anti-virally effective amount of the compounds according to the invention.

The present invention furthermore provides medicaments comprising at least one compound according to the invention and at least one or more further active compounds, in particular for the treatment and/or prophylaxis of the disorders mentioned above. Active compounds which may be mentioned by way of example and by way of preference as being suitable for combinations are: antiviral active compounds, such as gancyclovir or acyclovir.

The compounds according to the invention can act systemically and/or locally. For this purpose, they can be administered in a suitable way, such as, for example, by the oral, parenteral, pulmonary, nasal, sublingual, lingual, buccal, rectal, dermal, transdermal, conjunctival or otic route, or as implant or stent.

For these administration routes, it is possible to administer the active compounds in suitable administration forms.

Suitable for oral administration are administration forms which work as described in the prior art and deliver the active compounds rapidly and/or in modified form, which comprise the compounds according to the invention in crystalline and/ or amorphous and/or dissolved form, such as, for example, tablets (uncoated and coated tablets, for example tablets provided with enteric coatings or coatings whose dissolution is delayed or which are insoluble and which control the release of the compound according to the invention), tablets which rapidly decompose in the oral cavity, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (for example intravenously, intraarterially, intracardially, intraspinally or intralumbarly) or with inclusion of absorption (for example intramuscularly, subcutaneously, intracutaneously, percutaneously or intraperitonealy). Administration forms suitable for parenteral administration are, inter alia, preparations for injection and infusion in the form of solutions, suspensions, emulsions, lyophilizates or sterile powders.

Examples suitable for other administration routes are, for example, pharmaceutical forms for inhalation (inter alia powder inhalers, nebulizers), nasal drops/solutions/sprays; tablets to be administered lingually, sublingually or buccally, films/wafers of capsules, suppositories, preparations for the eyes or ears, vaginal capsules, aqueous solutions (lotions, shaking mixtures), lipophilic suspensions, ointments, creams, transdermal therapeutic systems, milk, pastes, foams, dusting powders, implants or stents.

The active compounds according to the invention can be converted into the stated administration forms. This can take place in a manner known per se by mixing with inert non-toxic, pharmaceutically acceptable auxiliaries. These auxiliaries include, inter alia, carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides) and flavour- and/or odour-masking agents.

The present invention furthermore provides medicaments comprising at least one compound according to the invention, usually together with one or more inert non-toxic, pharmaceutically suitable auxiliaries, and their use for the purposes mentioned above.

In general, it has proved advantageous to administer on intravenous administration amounts of from about 0.001 to 10 mg/kg, preferably from about 0.01 to 5 mg/kg, of body weight to achieve effective results, and the dosage on oral administration is from about 0.01 to 50 mg/kg, preferably from 0.1 to 25 mg/kg, of body weight.

It may nevertheless be necessary, where appropriate, to deviate from the amounts mentioned, depending on the body weight, the administration route, the individual response to the active compound, the mode of preparation and the time or interval over which administration takes place. Thus, in some cases it may be sufficient to make do with less than the aforementioned minimal amount, whereas in other cases the upper limit mentioned must be exceeded. In the event of administration of larger amounts, it may be advisable to divide these into a plurality of individual doses over the day.

The percentage data in the following tests and examples are percentages by weight unless otherwise indicated; parts are parts by weight. Solvent ratios, dilution ratios and concentration data of liquid/liquid solutions are in each case based on volume.

A. EXAMPLES

| Abbreviations: | |
|---|---|
| BINAP | 2,2'-bis(diphenylphosphino)-1,1'-binaphthyl |
| $CDCl_3$ | deuterated chloroform |
| TLC | thin-layer chromatography |
| DCI | direct chemical ionization (in MS) |
| DCM | dichloromethane |
| DIEA | N,N-diisopropylethylamine |
| DMSO | dimethyl sulphoxide |
| DMF | N,N-dimethylformamide |
| EA | ethyl acetate |
| EI | electron impact ionization (in MS) |
| ESI | electrospray ionization (in MS) |
| m.p. | melting point |
| sat. | saturated |
| h | hour |
| HPLC | high-pressure, high-performance liquid chromatography |
| conc. | concentrated |
| LC-MS | liquid chromatography-coupled mass spectroscopy |
| LDA | lithium diisopropylamide |
| min | minutes |
| MS | mass spectroscopy |
| NMR | nuclear magnetic resonance spectroscopy |
| Pd-C | palladium-on-carbon |
| RP-HPLC | reverse phase HPLC |
| RT | room temperature |
| $R_t$ | retention time (in HPLC) |
| THF | tetrahydrofuran |

General LC-MS and HPLC Methods

Method 1 (HPLC): instrument: HP 1100 with DAD detection; column: Kromasil RP-18, 60 mm×2 mm, 3.5 µm; mobile phase A: 5 ml $HClO_4$/l of water, mobile phase B: acetonitrile; gradient: 0 min 2% B, 0.5 min 2% B, 4.5 min 90% B, 6.5 min 90% B; flow rate: 0.75 ml/min; temp.: 30° C.; UV detection: 210 nm.

Method 2 (HPLC, preparative separation): column: CromSil C18, 250×30; flow rate 50 ml/min; time per run: 38 min; detection at 210 nm; mobile phase A: water, mobile phase B:

acetonitrile; gradient: 10% B (3 min)→90% B (31 min)→90% B (34 min)→10% B (34.01 min).

Method 3 (HPLC, separation of enantiomers): commercial CSP: Daicel Chiralpak AD using mobile phase mixtures of isohexane and alcohols, such as ethanol and isopropanol, with diethylamine added in a ratio of 85:15:0.03 (v/v/v).

Method 4 (LCMS): instrument: Micromass TOF-MUX interface with 4 parallel injections, Waters 600; column: YMC-ODS-AQ, 50 mm×2.1 mm, 3.0 µm; mobile phase A: water+0.05% formic acid, mobile phase B: acetonitrile+0.05% formic acid; gradient: 0.0 min 100% A→0.2 min 100% A→2.9 min 30% A→3.1 min 10% A→4.5 min 10% A; oven: room temperature; flow rate: 0.8 ml/min; UV detection: 210 nm.

Method 5 (LCMS): instrument: Micromass Quattro LCZ, HP1100; column: Symmetry C18, 50 mm×2.1 mm, 3.5 µm; mobile phase A: acetonitrile+0.1% formic acid, mobile phase B: water+0.1% formic acid; gradient: 0.0 min 10% A→4.0 min 90% A→6.0 min 90% A; oven: 40° C.; flow rate: 0.5 ml/min; UV detection: 208-400 nm.

Method 6 (LCMS): instrument: Finnigan MAT 900S, TSP: P4000, AS3000, UV3000HR; column: Symmetry C 18, 150 mm×2.1 mm, 5.0 µm; mobile phase C: water, mobile phase B: water+0.3 g of 35% strength hydrochloric acid, mobile phase A: acetonitrile; gradient: 0.0 min 2% A→2.5 min 95% A→5 min 95% A; oven: 70° C.; flow rate: 1.2 ml/min; UV detection: 210 nm.

Method 7 (HPLC): instrument: HP 1100 with DAD detection; column: Kromasil RP-18, 60 mm×2 mm, 3.5 µm; mobile phase A: 5 ml HClO$_4$/l of water, mobile phase B: acetonitrile; gradient 0 min 2% B, 0.5 min 2% B, 4.5 min 90% B, 9 min 90% B; flow rate: 0.75 ml/min; oven: 30° C.; UV detection: 210 nm.

Starting Materials

General Procedure [A]

Esterification of 2-nitrocinnamic acids with methanol 517.7 mmol of 2-nitrocinnamic acid are initially charged in 600 ml of methanol, 20 drops of concentrated sulphuric acid are then added and the mixture is heated under reflux for 72 hours. After the reaction has ended (the reaction is monitored by TLC), the reaction solution is cooled in an ice bath. The crystals formed are filtered off with suction. The mother liquor is then concentrated slightly, and the crystals formed during this operation are filtered off with suction. Both fractions are combined and recrystallized from methanol at RT.

Example 1A

Methyl (2E)-3-(2-nitrophenyl)propenoate

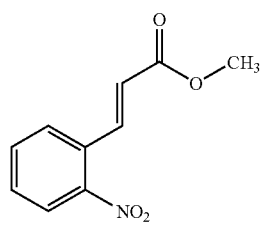

Starting with 100.0 g (517.7 mmol) of 2-nitrocinnamic acid, the general procedure [A] gives 72.6 g (68% of theory) of product.

HPLC (method 1): R$_t$=4.21 min

General Procedure [B]

Reduction of the Nitro Group of the 2-Nitrocinnamic Acid Derivatives

Under argon, 25 mmol of the nitro compound and 125 mmol of tin(II) chloride dehydrate are initially charged in 60 ml of absolute ethanol in a 250 ml two-necked flask. This suspension is stirred under reflux for 30 minutes, and a clear solution is formed. The solution is then allowed to cool to room temperature and subsequently poured into ice-water. Using either solid sodium bicarbonate or a saturated sodium carbonate solution, the pH is adjusted to pH=7-8. 60 ml of ethyl acetate are then added, and the precipitated tin salts are filtered off through kieselguhr (a layer of a thickness of about 1 cm). The organic phase is separated off and the aqueous phase is re-extracted once with ethyl acetate. The organic phases are combined, washed once with saturated sodium chloride solution and dried over sodium sulphate, and the solvent is concentrated to about half of its original volume. Activated carbon corresponding to 1% of the weight of the nitro compound is then added, and the mixture is heated under reflux for 30 minutes (the colour of the solution changes). The activated carbon is filtered off and the solvent is removed. The residue is dried under high vacuum and, without further purification, used directly for the next step.

Example 2A

Methyl (2E)-3-(2-aminophenyl)propenoate

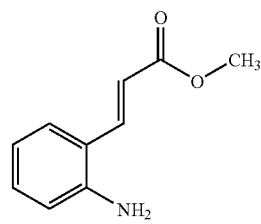

Starting with 15.00 g (72.34 mmol) of nitro compound, the general procedure [B] gives 12.05 g (94% of theory) of product.

HPLC (method 5): R$_t$=3.29 nm

General Procedure [C]

Synthesis of the Iminophosphoranes by Appel Reaction of the Substituted Anilines In a 50 ml one-necked flask, 10.0 mmol of the 2-aminocinnamic ester, 20.0 mmol of triethylphosphine, 100.0 mmol of carbon tetrachloride and 100.0 mmol of triethylamine are dissolved in 20 ml of acetonitrile. The mixture is stirred at room temperature for 2 hours. After the reaction has ended (the reaction is monitored by TLC or analytic HPLC), the solvent is removed under reduced pressure and the residue is purified by column chromatography on silica gel using cyclohexane/ethyl acetate=7:3.

Example 3A

Methyl (2E)-3-{2-[(triphenylphosphoranylidene)amino]phenyl}propenoate

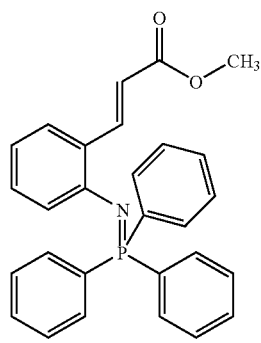

Starting with 2.00 g (11.28 mmol) of amine compound, the general procedure [C] gives, using 5.92 g (22.57 mmol) of triphenylphosphine, 4.42 g (90% of theory) of product.

HPLC (method 6): $R_t$=2.00 min
MS (ESI pos): m/z=428 (M+H)$^+$

General Procedure [D]

Synthesis of Phenylpiperazines by the Buchwald-Hartwig Reaction

To prepare for the reaction, the reaction flask is thoroughly dried by heating under high vacuum and vented with argon. 1.0 equivalent of the bromoaryl compound and 6.0 equivalents of piperazine in absolute toluene are initially charged in the flask (0.2-0.3M solution of the bromo compound). 0.01 equivalent of tris(dibenzylidene-acetone)dipalladium and 0.03 equivalent of BINAP are then added. The reaction mixture is stirred under reflux for 16 h. The mixture is then extracted once with water, the organic phase is extracted twice with 1N hydrochloric acid and the aqueous phase is adjusted to pH 8 using 1N aqueous sodium hydroxide solution and extracted three times with dichloromethane. The combined organic phases are dried over sodium sulphate and filtered, the solvent is removed under reduced pressure and the product is dried under high vacuum overnight.

Example 4A

N-(4-Fluoro-3-methylphenyl)piperazine

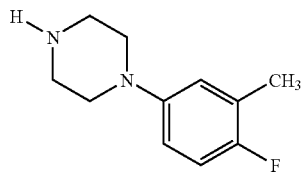

Starting with 5.0 g (26.5 mmol) of 4-fluoro-3-methyl-1-bromobenzene, the general procedure [D] gives 4.52 g (83% of theory) of product.

HPLC (method 1): $R_t$=3.54 min
MS (ESI pos): m/z=195 (M+H)$^+$

General Procedure [E]

Reaction of the Iminophosphorane with an Isocyanate and Subsequent Reaction with an Amine to Give the Dihydroquinazoline Derivative 1.0 equivalent of the iminophosphorane is dissolved in 20 ml of dichloromethane (0.1-0.2M solution). 1.05 equivalents of a substituted isocyanate are then added, and the mixture is stirred at RT until the reaction has ended. The reaction is monitored by TLC or by analytical HPLC.

1.0 equivalent of amine and a spatula tip of silica gel are then added to the resulting solution of the carbodiimide in dichloromethane, and the mixture is stirred at room temperature until the reaction has gone to completion. After the reaction has ended (reaction is monitored by TLC or HPLC), the mixture is concentrated and purified by preparative HPLC on an RP phase.

In certain cases, the NMR shows the presence of a varying proportion of non-cyclized reaction product. In these cases, the mixture of cyclized and non-cyclized product is taken up in dioxane, a spatula tip of silica gel is added and the mixture is stirred under reflux for 30 min to 16 h. The silica gel is filtered off and the solution is used for further reactions.

Example 5A

Methyl {2-[4-(4-fluorophenyl)-1-piperazinyl]-3-[3-(trifluoromethyl)phenyl]-3,4-dihydro-4-quinazolinyl}acetate

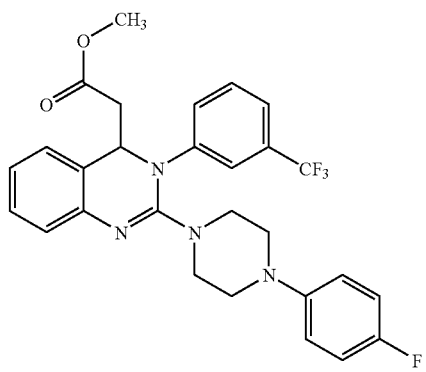

Starting with 5.0 g (11.43 mmol) of the iminophosphorane from Example 3A, 2.25 g (12.0 mmol) of trifluoro-m-tolyl isocyanate and 2.06 g (11.43 mmol) of N-(4-fluorophenyl)piperazine, the general procedure [E] gives 3.31 g (39% of theory) of product.

HPLC (method 1): $R_t$=4.72 min
MS (ESI pos): m/z=527 (M+H)$^+$

Example 6A

Methyl {2-[4-(4-fluorophenyl)-1-piperazinyl]-3-[3-(trifluoromethyl)phenyl]-3,4-dihydro-4-quinazolinyl}acetate

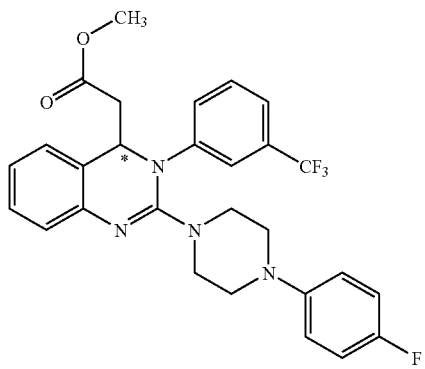

Starting with 300 mg of the methyl ester from Example 5A, separation of enantiomers (according to method 3) gives 125 mg of enantiomer A.

$\alpha_D^{20}$=+196.6 (C=0.53, CHCl$_3$)

Example 7A

Methyl {2-[4-(4-fluoro-3-methylphenyl)-1-piperazinyl]-3-[3-(trifluoromethyl)phenyl]-3,4-dihydro-4-quinazolinyl}acetate

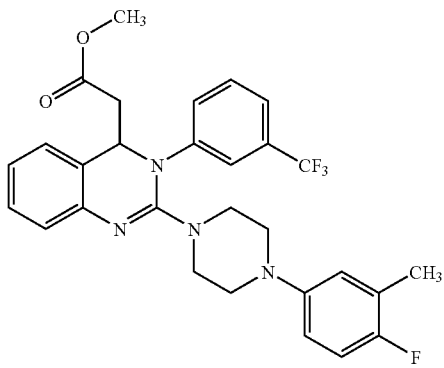

Starting with 200 mg (0.46 mmol) of the iminophosphorane from Example 3A, 90 mg (0.48 mmol) of trifluoro-m-tolyl isocyante and 89 mg (0.46 mmol) of the phenylpiperazine from Example 4A, the general procedure [E] and chromatographic purification (method 2) give 112 mg (43% of theory) of product.

HPLC (method 1): R$_f$=4.96 min

MS (ESI pos): m/z=541 (M+H)$^+$

Example 8A

Methyl {2-[4-(4-fluorophenyl)piperazin-1-yl]-3-[2-fluoro-5-(trifluoromethyl)phenyl]-3,4-dihydro-quinazolin-4-yl}acetate

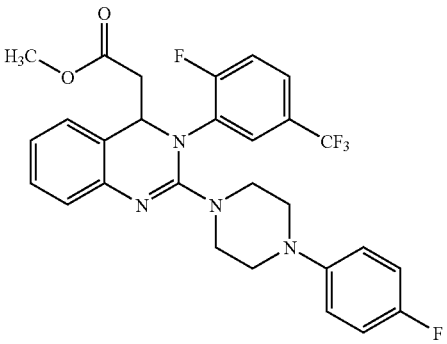

Starting with 150 mg (0.34 mmol) of the iminophosphorane from Example 3A, 74 mg (0.34 mmol) of 2-fluoro-5-(trifluoromethyl)phenyl isocyanate and 61 mg (0.34 mmol) of N-(4-fluorophenyl)piperazine, the general procedure [E] and chromatographic purification (method 2) give 34 mg (17% of theory) of product.

HPLC (method 1): R$_f$=4.73 min

MS (ESI pos): m/z=545 (M+H)$^+$

Example 9A

Methyl {2-[4-(3-chlorophenyl)piperazin-1-yl]-3-[2-fluoro-5-(trifluoromethyl)phenyl]-3,4-dihydro-quinazolin-4-yl}acetate

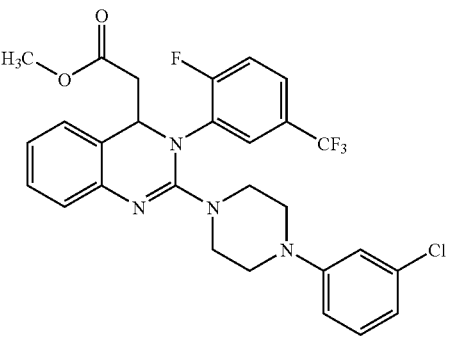

Starting with 150 mg (0.34 mmol) of the iminophosphorane from Example 3A, 74 mg (0.34 mmol) of 2-fluoro-5-(trifluoromethyl)phenyl isocyanate and 67 mg (0.34 mmol) of N-(3-chlorophenyl)piperazine, the general procedure [E] and chromatographic purification (method 2) give 95 mg (50% of theory) of product.

HPLC (method 1): R$_f$=4.91 min

MS (ESI pos): m/z=561 (M+H)$^+$

Example 10A

Methyl {2-[4-(4-fluorophenyl)piperazin-1-yl]-3-[4-fluoro-5-(trifluoromethyl)phenyl]-3,4-dihydro-quinazolin-4-yl}acetate

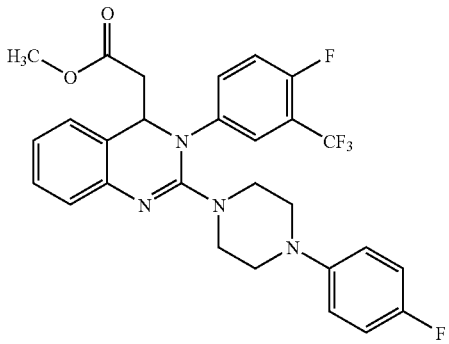

Starting with 150 mg (0.34 mmol) of the iminophosphorane from Example 3A, 74 mg (0.34 mmol) of 4-fluoro-3-(trifluoromethyl)phenyl isocyanate and 61 mg (0.34 mmol) of N-(4-fluorophenyl)piperazine, the general procedure [E] and chromatographic purification (method 2) give 111 mg (54% of theory) of product.

HPLC (method 1): $R_t$=4.87 min

MS (ESI pos): m/z=545 (M+H)$^+$

Example 11A

Methyl {2-[4-(3-chlorophenyl)piperazin-1-yl]-3-[2-methyl-4-chlorophenyl]-3,4-dihydroquinazolin-4-yl}acetate

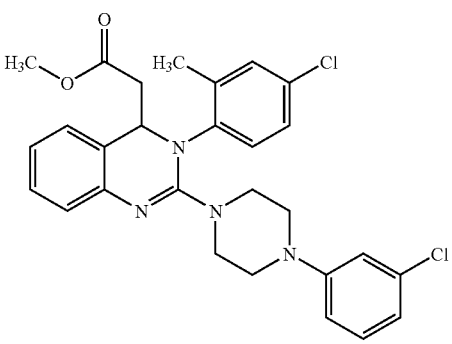

Starting with 150 mg (0.34 mmol) of the iminophosphorane from Example 3A, 60 mg (0.36 mmol) of 4-chloro-2-methylphenyl isocyanate and 67 mg (0.34 mmol) of N-(3-chlorophenyl)piperazine, the general procedure [E] and chromatographic purification (method 2) give 97 mg (46% of theory) of product.

HPLC (method 1): $R_t$=5.03 min

MS (ESI pos): m/z=523 (M+H)$^+$

Example 12A

2-Isocyanato-1-methoxy-4-(trifluoromethyl)benzene

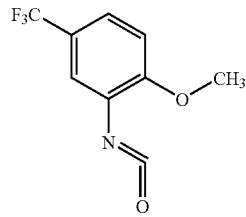

3 g (15.69 mmol) of 2-methoxy-5-trifluoromethylaniline are dissolved in 100 ml of dichloromethane, and 6.73 g (31.39 mmol) of 1,8-bis(dimethylamino)naphthalene are added. At 0-5° C., 2.24 g (11.3 mmol) of trichloromethyl chloroformate, dissolved in 50 ml of dichloromethane, are added dropwise, and the mixture is stirred at 0° C. for 30 min and at room temperature for 60 min. At 0° C., the mixture is washed with 1N hydrochloric acid, ice-water and sodium bicarbonate solution. Drying over magnesium sulphate and removal of the solvent by distillation gives the product. The isocyanate is then used in the subsequent reactions without further purification.

Yield: 3 g (88% of theory)

General Procedure [G]

Reaction of the Iminophosphorane with an Isocyanate to Give a Carbodiimide 1.0 equivalent of the iminophosphorane are dissolved in 20 ml of dichloromethane (0.1-0.2M solution). 1.05 equivalents of an isocyanate are then added, and the mixture is stirred at RT until the reaction has ended. The reaction is monitored by TLC or analytical HPLC. The solvent is then removed under reduced pressure, and the crude product is purified by chromatography on silica gel using cyclohexane/dichloromethane mixtures.

Example 13A (2E)-3-{2-[(iminomethylene)amino]phenyl}acrylic acid methyl ester 1-methoxy-2-methyl-4-(trifluoromethyl)benzene

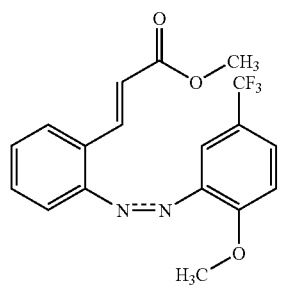

Starting with 2.0 g (4.57 mmol) of the iminophosphorane from Example 3A and 1.04 g (4.8 mmol) of the isocyanate from Example 12A, the general procedure [G] and chromatography with cyclohexane/dichloromethane (2:1 v/v, then 1:1 v/v) give 0.79 g (38% of theory) of product.

HPLC (method 1): $R_t$=5.52 min

Example 14A (2E)-3-{2-[(Iminomethylene)amino]phenyl}acrylic acid methyl ester 1-methoxy-2-methyl-4-chlorobenzene

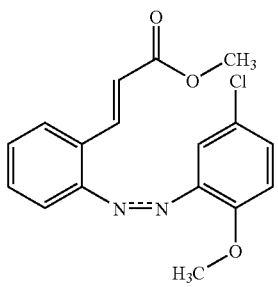

Starting with 2.0 g (4.57 mmol) of the iminophosphorane from Example 3A and 0.88 g (4.8 mmol) of 2-methoxy-5-chlorophenyl isocyanate, the general procedure [G] and chromatography with cyclohexane/dichloromethane (2:1 v/v, then 1:1 v/v) give 0.67 g (34% of theory) of product.

HPLC (method 1): $R_t$=5.53 min

Example 15A (2E)-3-{2-[(Iminomethylene)amino]phenyl}acrylic acid methyl ester 1-methoxy-2-methyl-4-methylbenzene

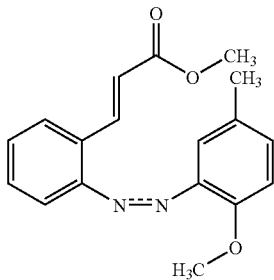

Starting with 2.0 g (4.57 mmol) of the iminophosphorane from Example 3A and 0.78 g (4.8 mmol) of 2-methoxy-5-methylphenyl isocyanate, the general procedure [G] and chromatography with cyclohexane/dichloromethane (2:1 v/v, then 1:1 v/v) give 0.85 g (57% of theory) of product.

HPLC (method 1): $R_t$=5.45 min

General Procedure [H]

Reaction of a Carbodiimide with a Phenylpiperazine to Give the Quinazoline 1.0 equivalent of the carbodiimide is dissolved in dioxane (0.1-0.25M solution). 1.0 equivalent of the phenylpiperazine is then added, silica gel is added to the mixture and the mixture is stirred under reflux of the solvent. The reaction is monitored by TLC or analytical HPLC. The solvent is then removed under reduced pressure and the crude product is purified by chromatography on silica gel using cyclohexane/ethyl acetate mixtures or by preparative HPLC (method 2).

Example 16A

Methyl {2-[4-(3-chlorophenyl)-1-piperazinyl]-3-[2-methoxy-5-(trifluoromethyl)phenyl]-3,4-dihydro-4-quinazolinyl}acetate

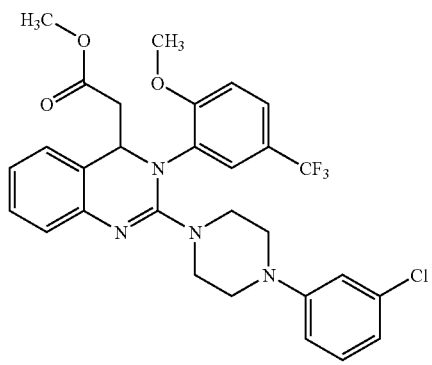

Starting with 160 mg (0.43 mmol) of the carbodiimide from Example 13A and 83.6 mg (0.43 mmol) of 3-chlorophenylpiperazine, the general procedure [H] gives 148 mg (61% of theory) of product.

HPLC (method 1): $R_t$=4.88 min

Example 17A

Methyl {2-[4-(3-methylphenyl)-1-piperazinyl]-3-[2-methoxy-5-(trifluoromethyl)phenyl]-3,4-dihydro-4-quinazolinyl}acetate

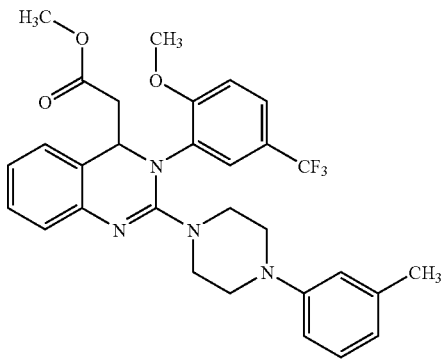

Starting with 150 mg (0.40 mmol) of the carbodiimide from Example 13A and 70 mg (0.40 mmol) of 3-methylphenylpiperazine, the general procedure [H] gives 159 mg (72% of theory) of product.

HPLC (method 1): $R_f$=4.79 min

Example 18A

Methyl {2-[4-(3-methoxyphenyl)-1-piperazinyl]-3-[2-methoxy-5-chlorophenyl]-3,4-dihydro-4-quinazolinyl}acetate

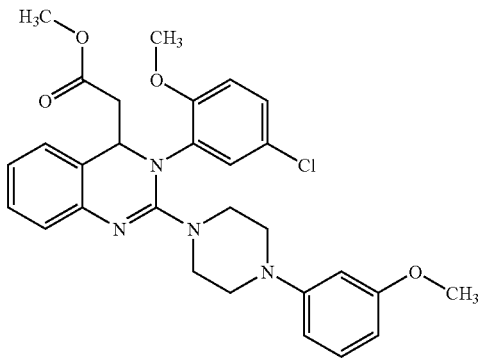

Starting with 100 mg (0.29 mmol) of the carbodiimide from Example 14A and 56 mg (0.29 mmol) of 3-methoxyphenylpiperazine, the general procedure [H] gives 115 mg (74% of theory) of product.

HPLC (method 1): $R_f$=4.7 min

Example 19A

Methyl {2-[4-(4-fluorophenyl)-1-piperazinyl]-3-[2-methoxy-5-chlorophenyl]-3,4-dihydro-4-quinazolinyl}acetate

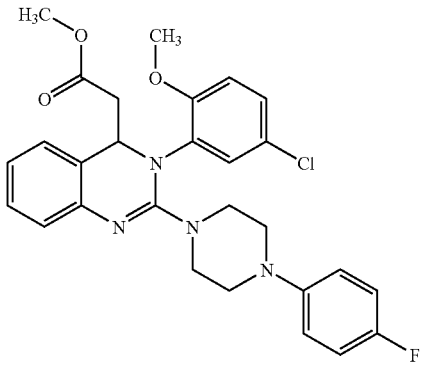

Starting with 100 mg (0.29 mmol) of the carbodiimide from Example 14A and 53 mg (0.29 mmol) of 4-fluorophenylpiperazine, the general procedure [H] gives 108 mg (71% of theory) of product.

HPLC (method 1): $R_f$=4.68 min

Example 20A

Methyl {2-[4-(3-methylphenyl)-1-piperazinyl]-3-[2-methoxy-5-methylphenyl]-3,4-dihydro-4-quinazolinyl}acetate

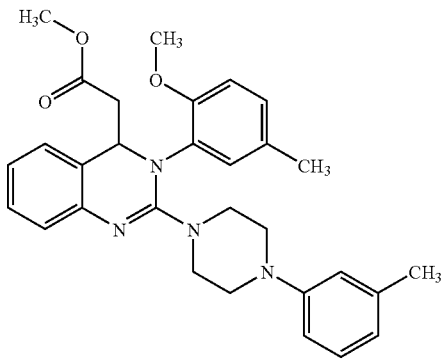

Starting with 160 mg (0.50 mmol) of the carbodiimide from Example 15A and 87 mg (0.50 mmol) of 3-methylphenylpiperazine, the general procedure [H] gives 205 mg (83% of theory) of product.

HPLC (method 1): $R_f$=4.93 min

Example 21A

Methyl {2-[4-(3-chlorophenyl)-1-piperazinyl]-3-[2-methoxy-5-methylphenyl]-3,4-dihydro-4-quinazolinyl}acetate

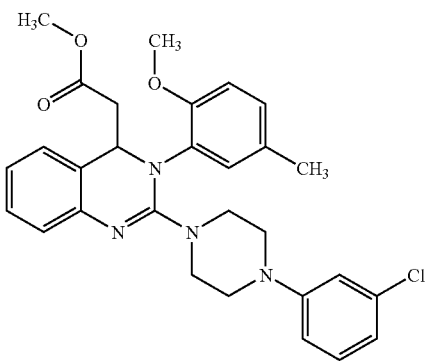

Starting with 160 mg (0.50 mmol) of the carbodiimide from Example 15A (WTB3297) and 98 mg (0.50 mmol) of 3-chlorophenylpiperazine, the general procedure [H] gives 207 mg (80% of theory) of product.

HPLC (method 1): $R_t$=5.04 min

WORKING EXAMPLES

General Procedure [F]

Hydrolysis of the Quinazolylacetic Acid Esters 1.0 equivalent of the quinazolylacetic acid ester is dissolved in dioxane, and 5.0 equivalents of 1N aqueous sodium hydroxide solution are added. The mixture is stirred at 100° C. for 16 hours, and after reaction has ended (the reaction is monitored by analytical HPLC) the mixture is concentrated. The residue is then taken up in water and adjusted to pH 5 using 1N hydrochloric acid. The resulting precipitate is filtered off, washed with a little water and diethyl ether and dried at room temperature under high vacuum. If the purity of the product is not high enough, the product is purified by preparative HPLC on an RP phase (method 2).

Example 1

{2-[4-(4-Fluoro-3-methylphenyl)-1-piperazinyl]-3-[3-(trifluoromethyl)phenyl]-3,4-dihydro-4-quinazolinyl}acetic acid

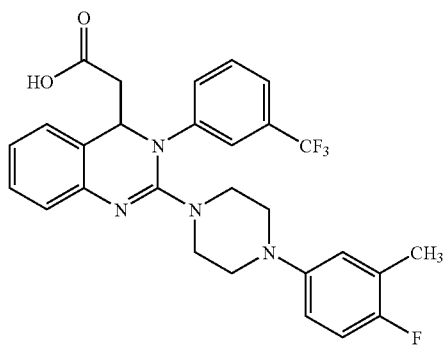

Starting with 98 mg (0.181 mmol) of the methyl ester from Example 7A, the general procedure [F] gives 66.4 mg (61% of theory) of product.

HPLC (method 1): $R_t$=4.69 min

MS (ESI pos): m/z=527 (M+H)$^+$ $^1$H-NMR (400 MHz, CD$_3$CN): δ [ppm]=7.75 (s, 1H), 7.67, (d, 1H), 7.57-7.56 (m, 3H), 7.37 (dt, 1H), 7.22-7.15 (m, 2H), 6.87 (t, 1H), 6.73 (dd, 1H), 6.64-6.60 (m, 1H), 5.36-5.32 (m, 1H), 3.70-3.53 (m, 4H), 3.10-2.96 (m, 5H), 2.67 (dd, 1H), 2.18 (d, 3H).

Example 2

{2-[4-(4-Fluorophenyl)-1-piperazinyl]-3-[2-fluoro-5-(trifluoromethyl)phenyl]-3,4-dihydro-4-quinazolinyl}acetic acid hydrochloride

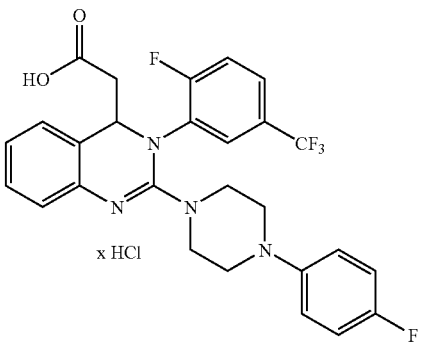

Starting with 30 mg (0.055 mmol) of the corresponding methyl ester, the general procedure [F] gives 20 mg (56% of theory) of product.

HPLC (method 1): $R_t$=4.5 min

MS (ESI pos): m/z=531 (M+H)$^+$ $^1$H-NMR (400 MHz, CD$_3$CN): δ [ppm]=8.11 (d, 1H); 7.59-7.56 (m, 1H); 7.31-7.23 (m, 3H); 7.12 (d, 1H); 7.04 (t, 1H); 6.96 (t, 2H); 6.83-6.79 (m, 2H); 5.12 (t, 1H); 3.59-3.48 (m, 4H); 2.92-2.80 (m, 5H); 2.59 (dd, 1H).

Example 3

{2-[4-(3-Chlorophenyl)-1-piperazinyl]-3-[2-fluoro-5-(trifluoromethyl)phenyl]-3,4-dihydro-4-quinazolinyl}acetic acid hydrochloride

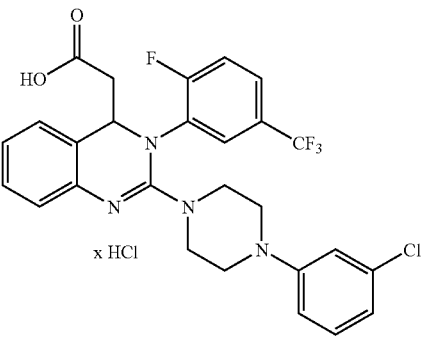

Starting with 90 mg (0.16 mmol) of the corresponding methyl ester, the general procedure [F] gives 24 mg (26% of theory) of product.

HPLC (method 1): $R_t$=4.63 min

MS (ESI pos): m/z=527 (M+H)$^+$ $^1$H-NMR (400 MHz, CD$_3$CN): δ [ppm]=7.87 (d, 1H); 7.50-7.48 (m, 1H); 7.26-7.21 (m, 2H); 7.17 (t, 1H); 7.14-7.12 (m, 1H); 7.05 (dd, 1H); 6.97 (dt, 1H); 6.84 (t, 1H); 6.80-6.77 (m, 2H); 5.01 (dd, 1H); 3.57-3.42 (m, 4H); 3.05-2.99, 2.97-2.85 (2x m, 4H); 2.79 (dd, 1H); 2.53 (dd, 1H).

Example 4

{2-[4-(4-Fluorophenyl)-1-piperazinyl]-3-[4-fluoro-3-(trifluoromethyl)phenyl]-3,4-dihydro-4-quinazolinyl}acetic acid hydrochloride

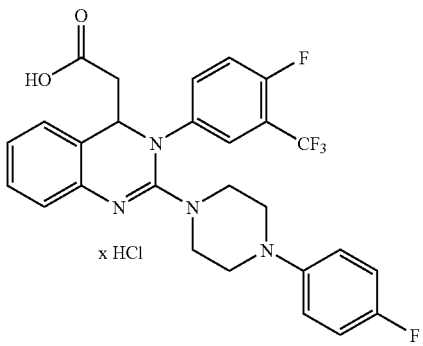

Starting with 95 mg (0.17 mmol) of the corresponding methyl ester, the general procedure [F] gives 27 mg (26% of theory) of product.

HPLC (method 1): $R_t$=4.56 min

MS (ESI pos): m/z=531 (M+H)$^+$ $^1$H-NMR (400 MHz, CD$_3$CN): δ [ppm]=7.64-7.62 (m, 1H); 7.58 (s, 1H); 7.36-7.31 (m, 1H); 7.24-7.16 (m, 2H); 7.11 (d, 1H); 7.05 (d, 1H); 7.01-6.95 (m, 3H); 6.91-6.87 (m, 2H); 5.12 (dd, 1H); 3.59-3.49 (m, 4H); 3.01-2.85 (m, 4H); 2.70 (dd, 1H); 2.53 (dd, 1H).

Example 5

{2-[4-(4-Fluorophenyl)-1-piperazinyl]-3-[3-(trifluoromethyl)phenyl]-3,4-dihydro-4-quinazolinyl}acetic acid hydrochloride

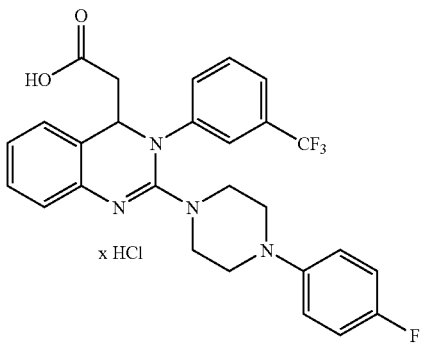

Starting with 3.31 g (6.29 mmol) of the methyl ester from Example 5A, the general procedure [F] gives 2.68 g (83% of theory) of product.

HPLC (method 1): $R_t$=4.62 min

MS (ESI pos): m/z=513 (M+H)$^+$ $^1$H-NMR (400 MHz, CD$_3$CN): δ [ppm]=7.57 (s, 1H); 7.45 (t, 1H); 7.37-7.34 (t, 2H); 7.21 (t, 1H); 7.10 (d, 1H); 7.06 (d, 1H); 7.00-6.92 (m, 3H); 6.89-6.86 (m, 2H); 5.19 (m, 1H); 3.60-3.49 (m, 4H); 3.01-2.87 (m, 4H); 2.72 (dd, 1H); 2.54 (dd, 1H).

Example 6

{2-[4-(3-Chlorophenyl)-1-piperazinyl]-3-[4-chloro-2-methylphenyl]-3,4-dihydro-4-quinazolinyl}acetic acid

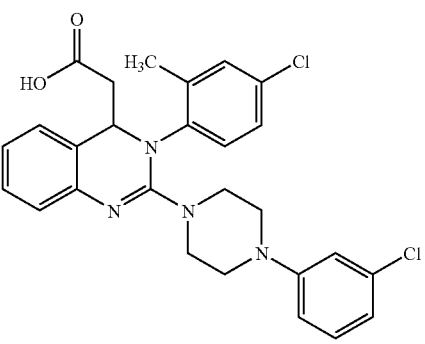

Starting with 90 mg (0.172 mmol) of the corresponding methyl ester, the general procedure [F] gives 71 mg (70% of theory) of product.

HPLC (method 1): $R_t$=4.75 min

MS (ESI pos): m/z=509 (M+H)$^+$ $^1$H-NMR (400 MHz, CD$_3$CN): δ [ppm]=7.72-7.63 (m, 2H); 7.41-7.34 (m, 2H); 7.21-7.14 (m, 6H); 6.80-6.72 (m, 4H); 5.10-5.06 (m, 1H); 3.59 (s, 4H); 3.13-2.91 (m, 5H); 2.74-2.68 (m, 1H); 1.68 (s, 3H).

Example 7

{2-[4-(4-Fluorophenyl)-1-piperazinyl]-3-[3-(trifluoromethyl)phenyl]-3,4-dihydro-4-quinazolinyl}acetic acid hydrochloride

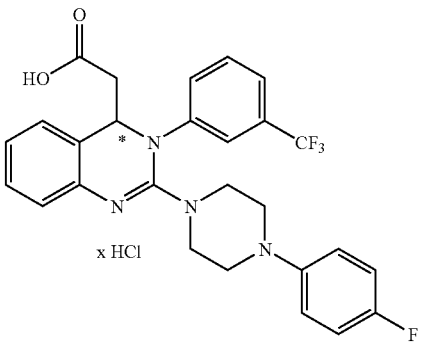

Starting with 120 mg (0.23 mmol) of the methyl ester from Example 6A, the general procedure [F] gives 100 mg of product (81% of theory).

HPLC (method 1): $R_t$=4.62 min

MS (ESI pos): m/z=513 (M+H)$^+$

Examples 8 to 25 of Table 1 can be prepared according to the general procedure [F].

TABLE 1

| Ex. No. | Structure | MW | R_t [min] | HPLC method | MS |
|---|---|---|---|---|---|
| 8 | 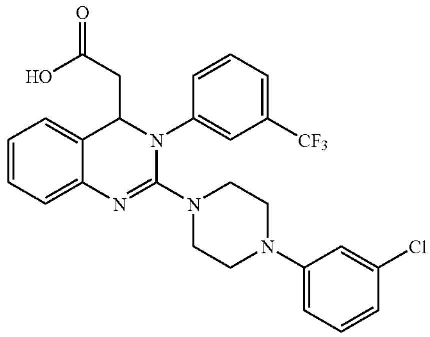 | 529.0 | 3.22 | 4 | 529 (M + H) |
| 9 | x HCl | 533.4 | 4.63 | 1 | 497 (M − HCl + H) |
| 10 | 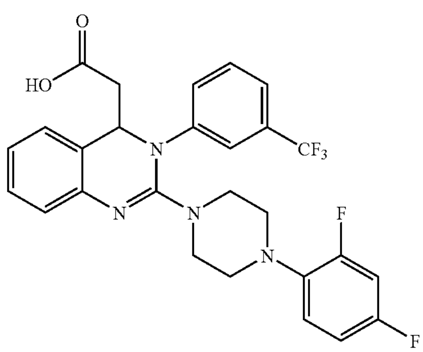 | 530.5 | 3.21 | 4 | 531 (M + H) |
| 11 | x HCl | 579.0 | 3.40 | 5 | 542 (M − HCl + H) |

TABLE 1-continued
| Ex. No. | Structure | MW | R$_t$ [min] | HPLC method | MS |
|---|---|---|---|---|---|
| 12 | 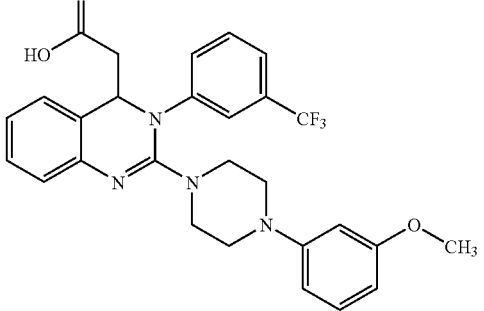 | 524.5 | 3.13 | 4 | 525 (M + H) |
| 13 | 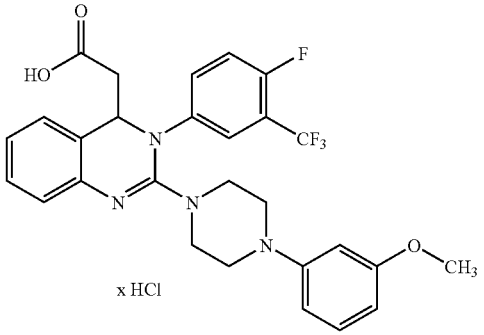 x HCl | 579.0 | 4.54 | 1 | 543 (M − HCl + H) |
| 14 | 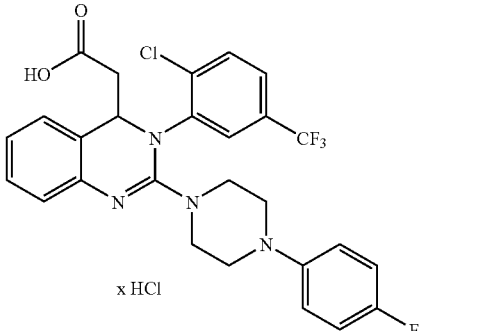 x HCl | 583.4 | 4.58 | 1 | 547 (M − HCl + H) |
| 15 | 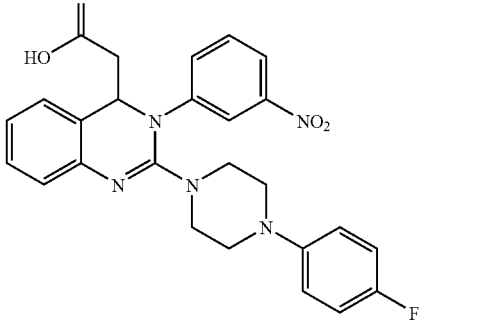 | 489.5 | 4.26 | 1 | 490 (M + H) |

TABLE 1-continued

| Ex. No. | Structure | MW | R$_t$ [min] | HPLC method | MS |
|---|---|---|---|---|---|
| 16 | 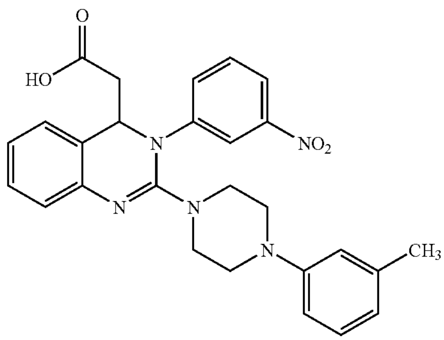 | 508.5 | 3.23 | 4 | 509 (M + H) |
| 17 | x HCl | 538.0 | 4.27 | 1 | 502 (M − HCl + H) |
| 18 | x HCl | 545.4 | 4.61 | 1 | 509 (M − HCl + H) |
| 19 | x HCl | 549.9 | 4.81 | 1 | 513 (M − HCl + H) |

TABLE 1-continued

| Ex. No. | Structure | MW | R$_t$ [min] | HPLC method | MS |
| --- | --- | --- | --- | --- | --- |
| 20 | (structure) x HCl | 542.4 | 4.46 | 1 | 506 (M − HCl + H) |
| 21 | (structure) x HCl | 529.4 | 4.57 | 1 | 493 (M − HCl + H) |
| 22 | (structure) | 494.5 | 3.12 | 4 | 495 (M + H) |
| 23 | (structure) x HCl | 518.0 | 4.19 | 1 | 482 (M − HCl + H) |

TABLE 1-continued

| Ex. No. | Structure | MW | R$_t$ [min] | HPLC method | MS |
|---|---|---|---|---|---|
| 24 | 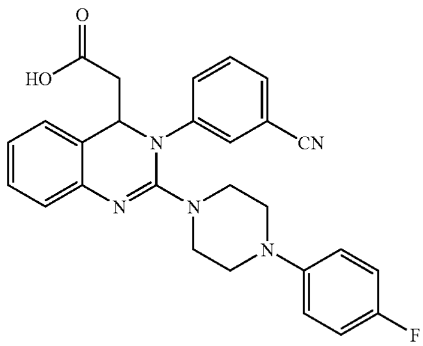 | 469.5 | 4.18 | 1 | 470 (M + H) |
| 25 | 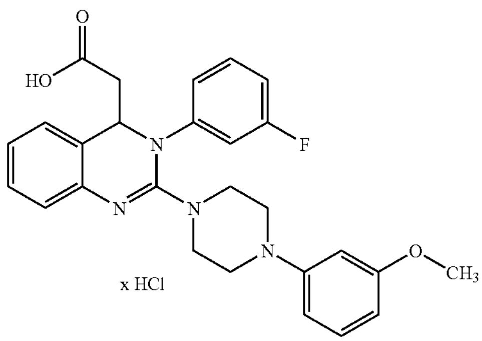 | 511.0 | 4.46 | 1 | 475 (M − HCl + H) |

Example 26

{2-[4-(3-Chlorophenyl)-1-piperazinyl]-3-[2-methoxy-5-(trifluoromethyl)phenyl]-3,4-dihydro-4-quinazolinyl)acetic acid

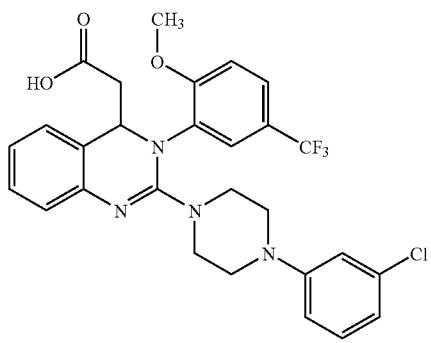

Starting with 135 mg (0.24 mmol) of the methyl ester from Example 16A, the general procedure [F] and purification by preparative HPLC give 106 mg (80% of theory) of product.

HPLC (method 1): R$_t$=4.82 min

MS (ESI pos): m/z=559 (M+H)$^+$ $^1$H-NMR (400 MHz, CD$_3$CN): δ [ppm]=8.21 (s, 0.5H); 7.77 (s$_b$, 0.5H); 7.52 (d, 1H); 7.22-7.07 (m, 5H); 6.98 (t, 1H); 6.79-6.76 (m, 2H); 6.71 (d, 1H); 4.96 (t, 1H); 3.76 (s$_b$, 3H); 3.49-3.33 (m, 6H); 2.98-2.92 (m, 2H); 2.84-2.78 (m, 2H).

Example 27

{2-[4-(3-Methylphenyl)-1-piperazinyl]-3-[2-methoxy-5-(trifluoromethyl)phenyl]-3,4-dihydro-4-quinazolinyl}acetic acid

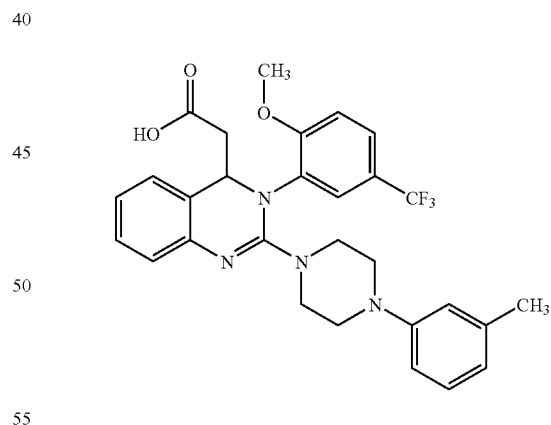

Starting with 120 mg (0.2 mmol) of the methyl ester from Example 17A, the general procedure [F] and purification by preparative HPLC give 55 mg (47% of theory) of product.

HPLC (method 7): R$_t$=4.57 min

MS (ESI neg): m/z=537 (M−H)$^-$ $^1$H-NMR (400 MHz, CD$_3$CN): δ [ppm]=8.23 (s, 0.4H); 7.77 (s$_b$, 0.4H); 7.52 (d, 1H); 7.22-7.04 (m, 5H); 6.96 (t, 1H); 6.65-6.62 (m, 2H); 6.58 (d, 1H); 4.96 (t, 1H); 3.76 (s$_b$, 3H); 3.49-3.33 (m, 4H); 2.92-2.68 (m, 5H); 2.56-2.51 (m, 1H).

Example 28

{2-[4-(3-Methoxyphenyl)-1-piperazinyl]-3-[2-methoxy-5-chlorophenyl]-3,4-dihydro-4-quinazolinyl]acetic acid

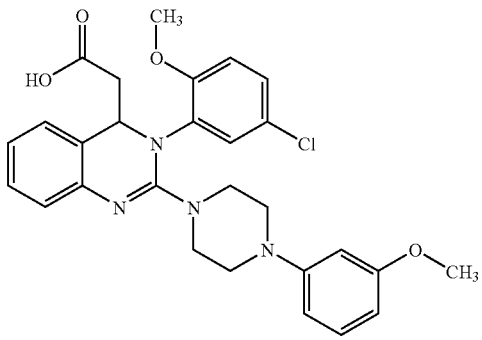

Starting with 120 mg (0.2 mmol) of the methyl ester from Example 18A, the general procedure [F] and purification by preparative HPLC give 55 mg (47% of theory) of product.

HPLC (method 1): $R_t$=4.40 min

MS (ESI neg): m/z=519 (M−H)⁻

¹H-NMR (400 MHz, CD$_3$CN): δ [ppm]=8.21 (s, 0.5H); 7.41 (s$_b$, 0.5H); 7.22-7.16 (m, 3H); 7.11-7.06 (m, 2H); 6.98 (t, 1H); 6.95 (t, 1H); 6.71 (d, 1H); 6.41-6.37 (m, 2H); 6.34 (t, 1H); 4.93 (t, 1H); 3.71 (s, 3H); 3.66 (s$_b$, 3H); 3.48-3.42 (m, 4H); 2.97-2.75 (m, 5H); 2.54-2.48 (m, 1H).

Example 29

{2-[4-(4-Fluorophenyl)-1-piperazinyl]-3-[2-methoxy-5-chlorophenyl]-3,4-dihydro-4-quinazolinyl}acetic acid

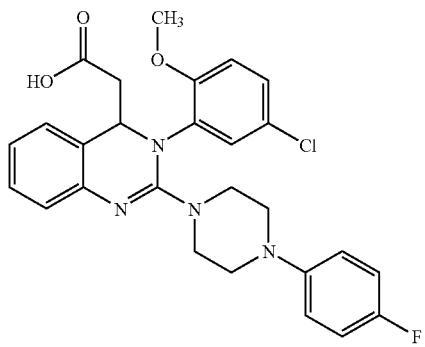

Starting with 94 mg (0.18 mmol) of the methyl ester from Example 19A, the general procedure [F] and purification by preparative HPLC give 6 mg (7% of theory) of product.

HPLC (method 7): $R_t$=4.43 min

MS (ESI pos): m/z=509 (M+H)⁺

¹H-NMR (400 MHz, CD$_3$CN): δ [ppm]=8.11 (s, 0.5H); 7.23-7.09 (m, 4H); 7.13-6.96 (m, 6.5H); 6.87-6.82 (m, 2H); 4.84 (t, 1H); 3.72 (s, 3H); 3.48-3.42 (m, 4H); 2.93-2.87 (m, 2H); 2.83-2.77 (m, 1H); 2.47 (dd, 1H). A further proton is presumed to be under the H$_2$O signal of the solvent (about 2.4-2.1 ppm).

Example 30

{2-[4-(3-Methylpheny)-1-piperazinyl]-3-[2-methoxy-5-methylphenyl]-3,4-dihydro-4-quinazolinyl}acetic acid

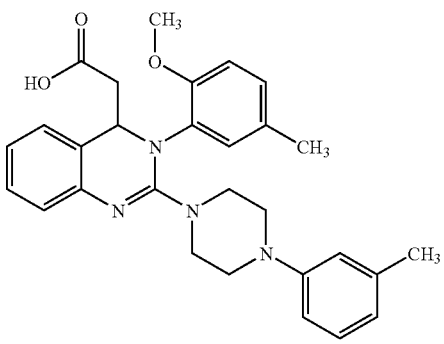

Starting with 181 mg (0.36 mmol) of the methyl ester from Example 20A, the general procedure [F] and purification by preparative HPLC give 158 mg (86% of theory) of product.

HPLC (method 7): $R_t$=4.63 min

MS (ESI pos): m/z=485 (M+H)⁺

¹H-NMR (400 MHz, CD$_3$CN): δ [ppm]=8.31 (s, 0.5H); 7.21-6.98 (m, 6H); 6.87-6.83 (m, 1H); 6.65-6.62 (m, 2H); 6.57 (d, 1H); 4.96-4.92 (m, 1H); 3.62 (s$_b$, 3H); 3.47-3.38 (m, 4H); 2.93-2.87 (m, 2H); 2.23 (s, 3H). The signals of further protons are presumed to be under the H$_2$O signal of the solvent (about 2.8-2.5 ppm).

Example 31

{2-[4-(3-Chlorophenyl)-1-piperazinyl]-3-[2-methoxy-5-methylphenyl]-3,4-dihydro-4-quinazolinyl}acetic acid

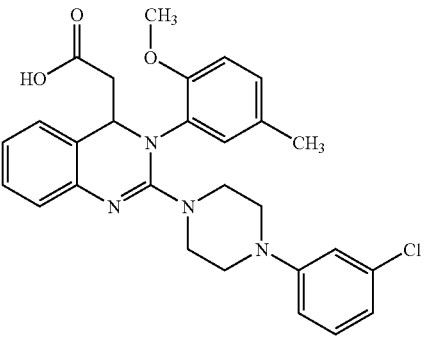

Starting with 182 mg (0.36 mmol) of the methyl ester from Example 21A, the general procedure [F] and purification by preparative HPLC give 160 mg (88% of theory) of product.

HPLC (method 7): $R_t$=4.78 min

MS (ESI pos): m/z=505 (M+H)⁺

¹H-NMR (400 MHz, CD$_3$CN): δ [ppm]=8.27 (s, 0.5H); 7.21-7.10 (m, 4.5H); 7.05-6.97 (m, 2H); 6.88-6.84 (m, 1H);

6.79-6.76 (m, 2H); 6.71 (d, 1H); 4.95-4.90 (m, 1H); 3.64 ($s_b$, 3H); 3.46-3.36 (m, 4H); 3.00-2.93 (m, 2H); 2.83-2.76 (m, 2H); 2.21 (s, 3H). The signals of further protons are presumed to be under the $H_2O$ signal of the solvent (about 2.8-2.5 ppm).

B. Assessment of the Physiological Activity

The in vitro effect of the compounds of the invention can be shown in the following assays:
Anti-HCMV (Anti-Human Cytomegalovirus) Cytopathogenicity Tests The test compounds are employed as 50 millimolar (mM) solutions in dimethyl sulphoxide (DMSO). Ganciclovir®, Foscarnet® and Cidofovir® are used as reference compounds. After addition of in each case 2 µl of the 50, 5, 0.5 and 0.05 mM DMSO stock solutions to 98 µl portions of cell culture medium in row 2 A-H for duplicate determinations, 1:2 dilutions are carried out with 50 µl portions of medium up to row 11 of the 96-well plate. The wells in rows 1 and 12 each contain 50 µl of medium. In 150 µl of a suspension of $1 \times 10^4$ cells (human prepuce fibroblasts [NHDF]) are pipetted into each of the wells (row 1=cell control) and, in rows 2-12, a mixture of HCMV-infected and uninfected NHDF cells (M.O.I.=0.001-0.002), i.e. 1-2 infected cells per 1000 uninfected cells. Row 12 (without substance) serves as virus control. The final test concentrations are 250-0.0005 µM. The plates are incubated at 37° C./5% $CO_2$ for 6 days, i.e. until all the cells are infected in the virus controls (100% cytopathogenic effect [CPE]). The wells are then fixed and stained by adding a mixture of formalin and Giemsa's dye (30 minutes), washed with double-distilled water and dried in a drying oven at 50° C. The plates are then assessed visually using an overhead microscope (Plaque Multiplier from Technomara).

The following data can be acquired from the test plates:
$CC_{50}$ (NHDF)=substance concentration in µM at which no visible cytostatic effects on the cells are evident by comparison with the untreated cell control;
$EC_{50}$ (HCMV)=substance concentration in µM which inhibits the CPE (cytopathic effect) by 50% compared with the untreated virus control;
SI (selectivity index)=$CC_{50}$ (NHDF)/$EC_{50}$ (HCMV).

Representative in vitro data for the effects of the compounds of the invention are shown in Table A:

TABLE A

| Example No. | NHDF $CC_{50}$ [µM] | HCMV $EC_{50}$ [µM] | SI HCMV |
|---|---|---|---|
| 1 | 17 | 0.027 | 630 |
| 2 | 39 | 0.06 | 650 |
| 6 | 22 | 0.4 | 63 |
| 19 | 24 | 0.4 | 60 |
| 23 | 188 | 0.76 | 247 |
| 26 | 31 | 0.019 | 1650 |
| 27 | 188 | 0.13 | 1446 |
| 28 | 63 | 0.025 | 2520 |
| 29 | 125 | 0.07 | 1786 |
| 30 | 250 | 0.25 | 1000 |
| 31 | 63 | 0.14 | 450 |

The suitability of the compounds of the invention for the treatment of HCMV infections can be shown in the following animal model:
HCMV Xenograft Gelfoam® Model
Animals:
3-4-week old female immunodeficient mice (16-18 g), Fox Chase SCID or Fox Chase SCID-NOD or SCID beige, are purchased from commercial breeders (Taconic M+B, Jackson USA). The animals are housed under sterile conditions (including bedding and feed) in isolators.
Virus Growing:
Human cytomegalovirus (HCMV), Davis or AD169 strain, is grown in vitro on human embryonic prepuce fibroblasts (NHDF cells). After the NHDF cells have been infected with a multiplicity of infection (M.O.I.) of 0.01-0.03, the virus-infected cells are harvested 5-10 days later and stored in the presence of minimal essential medium (MEM), 10% fetal calf serum (FCS) with 10% DMSO at −40° C. After serial ten-fold dilutions of the virus-infected cells, the titre is determined on 24-well plates of confluent NHDF cells after vital staining with Neutral Red.
Preparation of the Sponges, Transplantation, Treatment and Evaluation:
Collagen sponges 1×1×1 cm in size (Gelfoam®; from Peasel & Lorey, order No. 407534; K. T. Chong et al., Abstracts of 39th Interscience Conference on Antimicrobial Agents and Chemotherapy, 1999, p. 439) are initially wetted with phosphate-buffered saline (PBS), the trapped air bubbles are removed by degassing, and then stored in MEM+10% FCS. $1 \times 10^6$ virus-infected NHDF cells (infection with HCMV Davis or HCMV AD169 M.O.I.=0.01) are detached 3 hours after infection and added in a drop of 20 µl of MEM, 10% of FCS, to a moist sponge. About 16 hours later, the infected sponges are incubated with 25 µl of PBS/0.1% BSA/1 mM DTT with 5 ng/µl basic fibroblast growth factor (bFGF). For the transplantation, the immunodeficient mice are anaesthetized with Avertin or a ketamine/xylazine/azepromazine mixture, the fur on the back is removed using a shaver, the epidermis is opened 1-2 cm, unstressed and the moist sponges are transplanted under the dorsal skin. The surgical wound is closed with tissue glue. 6 hours after the transplantation, the mice can be treated for the first time (on the day of the operation there is one treatment). The next days, over a period of 8 days, the mice are treated with substance orally three times a day (7.00 h and 14.00 h and 19.00 h), two times a day (8.00 h and 18.00 h) or once a day (14.00 h). The daily dose is, for example 3 or 10 or 30 or 60 or 100 mg/kg of body weight, the volume administered is 10 ml/kg of body weight. The substances are formulated in the form of a 0.5% strength Tylose suspension with 2% DMSO or a 0.5% strength Tylose suspension. 9 days after transplantation and 16 hours after the last administration of substance, the animals are painlessly sacrificed and the sponge is removed. The virus-infected cells are released from the sponge by collagenase digestion (330 U/1.5 ml) and stored in the presence of MEM, 10% fetal calf serum, 10% DMSO at −140° C. Evaluation takes place after serial ten-fold dilutions of the virus-infected cells by determining the titre on 24-well plates of confluent NHDF cells after vital staining with Neutral Red. The number of infectious virus particles after the substance treatment compared with the placebo-treated control is determined.

C. Exemplary Embodiments of Pharmaceutical Compositions

The compounds of the invention can be converted into pharmaceutical preparations in the following ways:
Tablet:
Composition:
100 mg of the compound of Example 1, 50 mg of lactose (monohydrate), 50 mg of corn starch (native), 10 mg of polyvinylpyrrolidone (PVP 25) (from BASF, Ludwigshafen, Germany) and 2 mg of magnesium stearate.

Tablet weight 212 mg. Diameter 8 mm, radius of curvature 12 mm.
Production:
The mixture of active ingredient, lactose and starch is granulated with a 5% strength solution (m/m) of the PVP in water. The granules are then dried and mixed with the magnesium stearate for 5 min. This mixture is compressed using a conventional tablet press (see above for format of the tablet). A guideline for the compressive force used for the compression is 15 kN.

Suspension Which Can be Administered Orally:
Composition:
1000 mg of the compound of Example 1, 1000 mg of ethanol (96%), 400 mg of Rhodigel (xanthan gum from FMC, Pennsylvania, USA) and 99 g of water.

10 ml of oral suspension are equivalent to a single dose of 100 mg of the compound of the invention.
Production:
The Rhodigel is suspended in ethanol, and the active ingredient is added to the suspension. The water is added while stirring. The mixture is stirred for about 6 h until the swelling of the Rhodigel is complete.

Solution Which Can be Administered Intravenously:
Composition:
1 mg of the compound of Example 1, 15 g of polyethylene glycol 400 and 250 g of water for injection.
Production:
The compound according to the invention is dissolved together with polyethylene glycol 400 in the water with stirring. The solution is sterilized by filtration (pore diameter 0.22 μm) and dispensed under aseptic conditions into heat-sterilized infusion bottles. The latter are closed with infusion stoppers and trimmed caps.

The invention claimed is:

1. A medicament comprising a compound of formula (I), or a salt, or a solvate, or a solvate of a salt thereof,

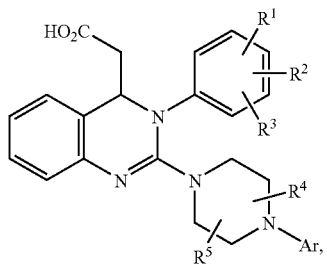

in which
Ar represents aryl which may be substituted by 1 to 3 substituents, where the substituents are selected independently of one another from the group consisting of alkyl, alkoxy, formyl, carboxyl, alkylcarbonyl, alkoxycarbonyl, trifluoromethyl, halogen, cyano, hydroxyl, amino, alkylamino, aminocarbonyl and nitro,
where alkyl may be substituted by 1 to 3 substituents, where the substituents are selected independently of one another from the group consisting of halogen, amino, alkylamino, hydroxyl and aryl,
or two of the substituents on the aryl radical together with the carbon atoms to which they are attached form a 1,3-dioxolane, a cyclopentane ring or a cyclohexane ring, and any third substituent present is selected independently therefrom from the group mentioned,
$R^1$ represents hydrogen, alkyl, alkoxy, cyano, halogen, nitro or trifluoromethyl,
$R^2$ represents hydrogen, alkyl, alkoxy, cyano, halogen, nitro or trifluoromethyl,
$R^3$ represents alkyl, alkoxy, cyano, halogen, nitro or trifluoromethyl
or
one of the radicals $R^1$, $R^2$ and $R^3$ represents hydrogen, alkyl, alkoxy, cyano, halogen, nitro or trifluoromethyl and the other two together with the carbon atoms to which they are attached form a 1,3-dioxolane, a cyclopentane ring or a cyclohexane ring,
$R^4$ represents hydrogen or alkyl,
$R^5$ represents hydrogen or alkyl,
or
the radicals $R^4$ and $R^5$ are attached to carbon atoms directly opposing each other in the piperazine ring and form a methylene bridge which is optionally substituted by 1 or 2 methyl groups, in combination with a further active compound.

2. The medicament according to claim 1, wherein the further active compound is an antiviral active compound.

3. The medicament according to claim 2, wherein the antiviral active compound is gancyclovir or acyclovir.

4. A method of controlling viral infections in humans and animals, said method comprising administering an antivirally effective amount of a medicament comprising a compound of formula (I) or a salt, or a solvate, or a solvate of a salt thereof,

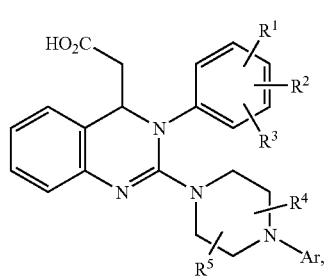

in which
Ar represents aryl which may be substituted by 1 to 3 substituents, where the substituents are selected independently of one another from the group consisting of alkyl, alkoxy, formyl, carboxyl, alkylcarbonyl, alkoxycarbonyl, trifluoromethyl, halogen, cyano, hydroxyl, amino, alkylamino, aminocarbonyl and nitro,
where alkyl may be substituted by 1 to 3 substituents, where the substituents are selected independently of one another from the group consisting of halogen, amino, alkylamino, hydroxyl and aryl,
or two of the substituents on the aryl radical together with the carbon atoms to which they are attached form a 1,3-dioxolane, a cyclopentane ring or a cyclohexane ring, and any third substituent present is selected independently therefrom from the group mentioned,
$R^1$ represents hydrogen, alkyl, alkoxy, cyano, halogen, nitro or trifluoromethyl,
$R^2$ represents hydrogen, alkyl, alkoxy, cyano, halogen, nitro or trifluoromethyl,
$R^3$ represents alkyl, alkoxy, cyano, halogen, nitro or trifluoromethyl
or
one of the radicals $R^1$, $R^2$ and $R^3$ represents hydrogen, alkyl, alkoxy, cyano, halogen, nitro or trifluoromethyl and the other two together with the carbon atoms to which they are attached form a 1,3-dioxolane, a cyclopentane ring or a cyclohexane ring,
$R^4$ represents hydrogen or alkyl,
$R^5$ represents hydrogen or alkyl,
or
the radicals $R^4$ and $R^5$ are attached to carbon atoms directly opposing each other in the piperazine ring and form a methylene bridge which is optionally substituted by 1 or 2 methyl groups, in combination with a further active compound.

* * * * *